United States Patent [19]

Herbert et al.

[11] 4,290,431
[45] Sep. 22, 1981

[54] TRANSCUTANEOUS OXYGEN AND LOCAL PERFUSION MEASUREMENT

[75] Inventors: Normand C. Herbert, Goffstown, N.H.; Richard S. Burwen, Lexington, Mass.; Richard A. Mentelos, Hamden, Conn.

[73] Assignee: Novametrix Medical Systems, Inc., Wallingford, Conn.

[21] Appl. No.: 50,691

[22] Filed: Jun. 21, 1979

[51] Int. Cl.³ .............................................. A61B 5/00
[52] U.S. Cl. ................................ 128/635; 204/195 B; 204/195 P; 219/209; 219/501
[58] Field of Search ................... 128/635, 632, 303.14, 128/399; 204/195 R, 195 B, 195 P, 195 M; 219/501, 209, 210

[56] References Cited

U.S. PATENT DOCUMENTS

| | | | |
|---|---|---|---|
| 3,308,221 | 3/1967 | Hilbiber | 219/501 |
| 3,320,407 | 5/1967 | Holmes | 219/501 |
| 3,450,863 | 6/1969 | Scholl | 219/501 |
| 3,789,853 | 2/1974 | Reinhard | 128/399 |
| 4,114,602 | 9/1978 | Huch et al. | 128/635 |
| 4,126,137 | 11/1978 | Archibald | 128/303.14 |

FOREIGN PATENT DOCUMENTS 1324662  7/1973  United Kingdom ............ 204/195 P

OTHER PUBLICATIONS

Vesterager, "Transcutaneous PO2 Electrode", Scand J. Clin. Lab. Invest., 37 (Supp. 146), 27–30, 1977.
Huch et al., "Transcutaneous Measurement of . . . PO2", J. Perinct. Med., 1 (1973), 183.
Vesterager, "Continuous Transcutaneous . . . PO2", *Measurement of O2*, 1976, pp. 260–269.
Eberhard et al., "Method for Cutaneous . . . presure", Biomed. Technik., vol. 18, No. 6, pp. 216–221, Dec. 1973.

*Primary Examiner*—Lee S. Cohen
*Attorney, Agent, or Firm*—Howard F. Mandelbaum

[57] ABSTRACT

An apparatus and method for measuring and monitoring blood oxygen content and local perfusion factor. A transcutaneous gas measurement probe is heated by application of an electric current to a semi-conductor device housed therein. The heat developed in a semi-conductor device heats the probe to a constant temperature under the control of a temperature monitoring and regulating circuit and the amount of power applied to the semi-conductor device is measured by multiplying the current conducted through the semiconductor device by the voltage across it to provide a measurement of local perfusion factor. An alerting device is provided to signal when blood oxygen content and local perfusion factor are outside a predetermined acceptable range.

8 Claims, 4 Drawing Figures

TRANSCUTANEOUS OXYGEN AND LOCAL PERFUSION MEASUREMENT

BACKGROUND OF THE INVENTION

This invention relates to transcutaneous oxygen probes used to sense and measure the amount of oxygen emitted at the skin surface of a living body. More specifically, the invention relates to such probes which have a surface permeable to oxygen which is adapted to engage the skin of the body and which have a heat conducting member and a means for heating the member in order to warm the skin for enhancing vasodilation of the blood vessels beneath the skin and thereby increase the degree of local blood circulation and local oxygen emission.

It is known in the medical art of non-invasive blood oxygen content monitoring and measurement to apply to the surface of the skin of the person whose blood oxygen content is to be monitored and measured, a probe having a barrier permeable to oxygen and impermeable to other gases soluble in an electrolyte solution stored above the membrane. In such a device, often referred to as a Clark electrode, a small voltage is applied between two electrodes having a gap which is bridged by the electrolyte solution and the current flow between the electrodes resulting from the ionization of the solution by the dissolved oxygen is measured. The magnitude of the current is directly proportional to the amount of oxygen escaping from the blood and through the skin at the region where the probe is applied.

It is also known in the prior art to enhance the sensitivity and accuracy of the measurement of oxygen contained in the blood by using a heating device to warm the skin in the region of application of the probe to promote vasodilation of the local blood vessels thereby increasing blood flow to the region of application and also increasing the percentage of blood oxygen emitted for sensing by the probe. U.S. Pat. No. 3,628,525 to Polanyi discloses a blood oxygenation and pulse monitoring apparatus which employs optical means to measure blood oxygen content and which includes a heating coil which heats a platen in engagement with the skin of the body to enhance vasodilation of the blood vessels to enhance the oxygen measurement.

Resistive heating devices such as heating coils have also been applied to transcutaneous oxygen probes of the Clark type to heat the skin and thereby increase the degree of transcutaneous oxygen emission. Examples of Clark type electrodes employing resistive heating means are found in U.S. Pat. No. 3,795,239 to Eberhard et al., for an electrochemical electrode with heating means, U.S. Pat. No. 3,998,212 to Reichenberger for an electrode for percutaneous polarographic measurements and U.S. Pat. No. 4,005,700 to Parker for a device for measuring blood gases. French Pat. No. 2,346,716 also discloses a Clark type electrode having a heating coil or sleeve to heat the electrode for maximizing the permeability of the skin to oxygen.

It is further known in the art that the degree of heat which must be applied to the skin in order to maintain the skin at a constant temperature, i.e. the temperature at which oxygen emission is optimal, can provide valuable information relative to blood circulation and blood pressure. It is therefore important to be able to accurately monitor and measure the amount of power which must be applied to heat the oxygen probe to maintain a constant skin temperature. The quantity of power needed to maintain constant skin temperature can be displayed or used to compute a numerical indicator of the power requirement. This is referred to as the local perfusion factor.

In order to derive a measure of the power applied to prior art heated electrodes which employ resistive elements for maintaining a desired elevated skin temperature, power must be computed from the relationship $P = I^2 R$ where P is the power applied, I is the current flowing through the coil and R is the resistance of the coil or $P = E^2/R$ where E is the voltage drop across the heating coil. In either of the above cases, it is necessary that a voltage or current quantity be squared and then multiplied by a resistance value. As a result of the squaring operation, the ratio of the terms to be multiplied (or divided) can be very large and will often exceed the maximum ratio of the multiplacand to multiplier permissible for accurate multiplication with commercially available mulplier circuits. This limitation, inherent in transcutaneous oxygen probes employing resistive heating devices, is believed responsible for the failure of such devices to take advantage of the valuable information available from the computation of local perfusion factor based on the quantity of power needed to maintain a constant probe temperature.

SUMMARY OF THE INVENTION

The instant invention overcomes the above stated problems of the prior art in providing a novel heated transcutaneous oxygen probe with which the amount of power applied to heat the probe can be accurately computed for display or computation of a factor indicative of local perfusion. More specifically, the present invention includes a transcutaneous gas measurement probe having a conductive housing comprising first and second electrodes, means for maintaining an electrolytic solution in contact with the electrodes, barrier means permeable to a gas to be measured and mounted on the probe to permit contact with the skin and permeation of the gas emitted from the skin into the electrolytic solution, and a semi-conductor device mounted within the probe in heat transmitting relationship therewith so as to heat the probe in response to application of an electric current to the semi-conductor device. A regulating circuit can be connected to the semi-conductor device for controlling the amount of current applied to the semi-conductor device for regulating or maintaining constant, the temperature of the probe which is in contact with and dependent upon the temperature of the skin. The invention further provides for the application of a power measurement computation and display circuit which can accurately compute the magnitude of power consumed by the semi-conductor device under the control of a thermostat functioning to maintain the temperature of the probe at a pre-determined constant level.

It is therefore an object of the invention to provide a transcutaneous oxygen probe which can be heated without the use of resistive heating elements to enhance vasodilation of proximate blood vessels and oxygen permeation through the skin.

Another object of the invention is to provide a heated transcutaneous oxygen probe including thermostat means for controlling the amount of power applied to the probe for maintaining the temperature of the probe at a constant predetermined level.

Still another object of the present invention is to provide a heated transcutaneous oxygen probe wherein the amount of power applied to or dissipated in the heating means, for maintaining the temperature of the probe constant at a predetermined level, can be computed with greater accuracy and at lesser expense than was heretofore possible with resistively heated probes.

Other and further objects of the invention will be apparent from the following drawings and description of a preferred embodiment of the invention in which like reference numerals are used to indicate like parts in the various views.

DESCRIPTION OF THE PREFERRED EMBODIMENT

Figure 1:
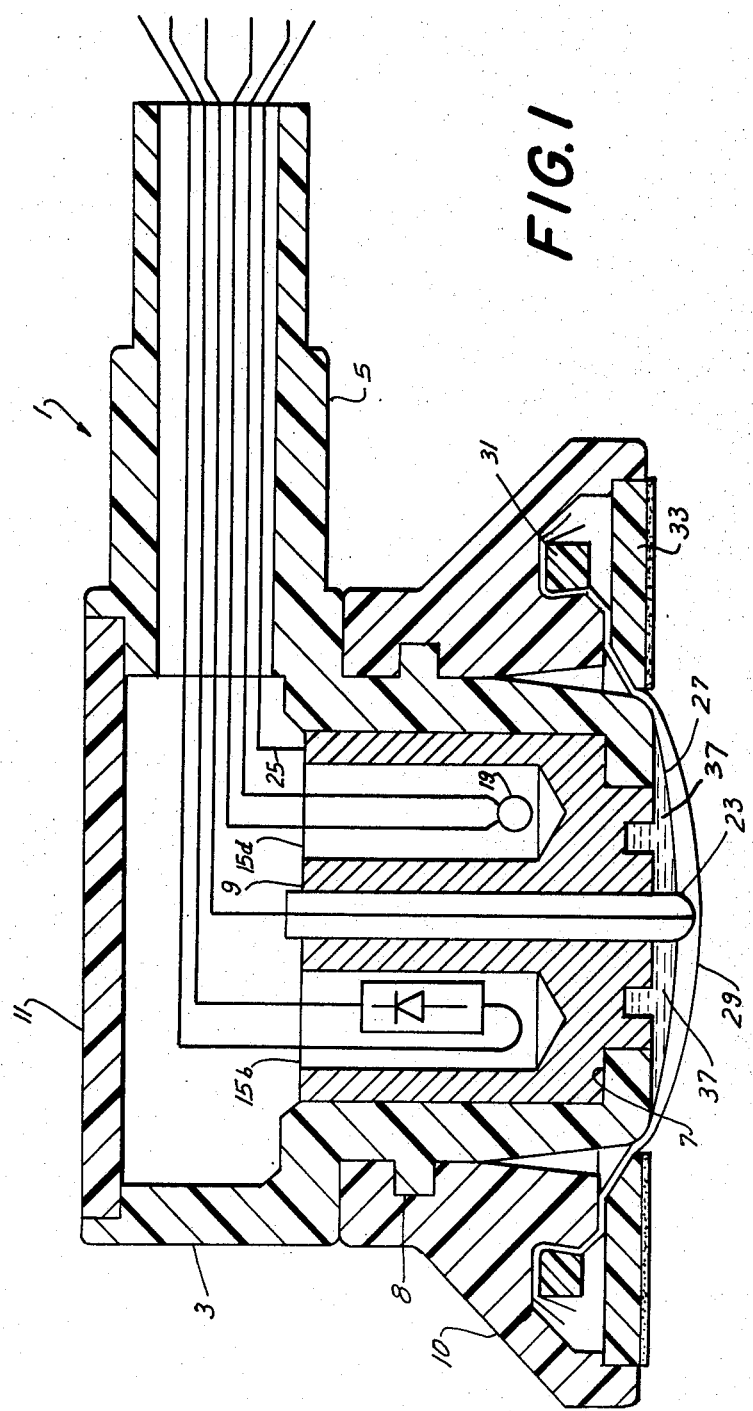
FIG. 1 is a sectional elevation view of the transcutaneous oxygen probe of the preferred embodiment of the invention.

Referring now to FIG. 1 of the drawings, there is shown a transcutaneous oxygen probe 1 according to the invention. The probe includes a housing formed from an outer irregularly shaped cylindrical shell 3, having a vertical axis in the view of FIG. 1, and further having an integrally molded lateral extension 5 with a cylindrical bore having a horizontal axis in the view of FIG. 1.

The shell 3 has a rapidly inwardly directed bottom defining a circular shoulder 7 in the interior of its bore. The shell 3 is provided on its exterior threads 8 adapted to mate with a removable fixation ring 10 having complementary threads on its interior and which will be more fully described.

Mounted within the shell 3 is substantially cylindrical mass 9 of a conductive metal which in the preferred embodiment of the invention is silver. Silver is chosen as a result of its superior electrical and heat conducting properties but other conductors, e.g. copper, having similar properties can be employed with acceptable results. The silver mass 9 has a constant outer diameter for the major portion of its length and a smaller diameter portion at one end thereby forming a circular shoulder to mate with the shoulder 7 of the shell 3 so that the silver mass 9 can be supported within the shell 3 with its lowermost surface in the view of FIG. 1 substantially in the same plane as the lowermost surface of the shell 3. A circular cover member 11 is fitted atop the shell 3 after insertion of the silver mass 9. The cover 11 may be welded in place or firmly secured by use of a known adhesive or a force fit or a combination of the foregoing.

Figure 2:
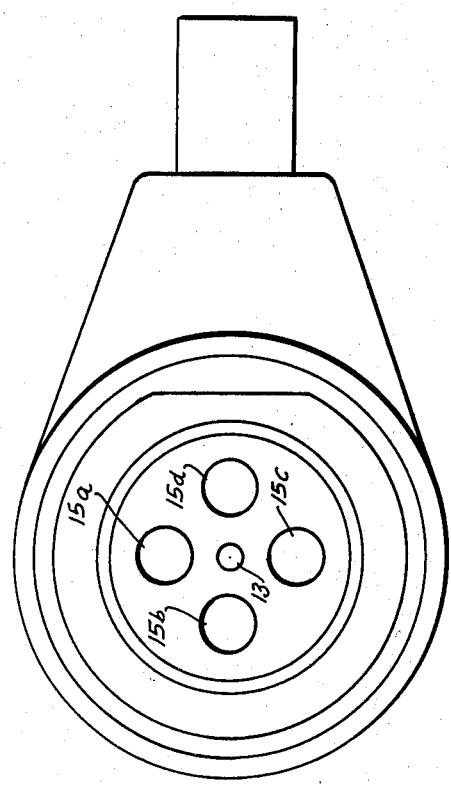
FIG. 2 is a plan view of the probe of FIG. 1 with top cover removed.

Referring additionally to FIG. 2, it is seen that the cylindrical silver mass 9 has an axial bore 13 throughout its length with an axis common to the axis of the cylindrical mass 9 and the shell 3. In addition, there are four larger axial bores 15a, 15b, 15c, and 15d, having respective axes parallel to and radially equidistant from the common axis of the central bore 13, cylindrical silver mass 9 and shell 3. The axial bores 15a-d are spaced at 90 degree intervals about the central bore 13.

The bores 15a-d partially penetrate the depth of the cylindrical mass 9, as can clearly be seen in FIG. 1. Bores 15a, b and c have mounted within each of them one diode with electrically conductive leads extending from the cathode and anode of each diode. The diodes 17a, 17b and 17c respectively disposed in the bores 15a-c are connected in series and the two leads extending from either end of the series chain of diodes 17a-c, extend through the horizontal bore of the lateral extension 5 of the shell 3 for connection to an external power supply and regulation circuit which will subsequently be described. Three diodes are used to heat the probe in the preferred embodiment to minimize power supply size. However, a single diode of appropriate selection can be utilized to heat the probe within the scope of the invention.

The axial bore 15d has disposed within it a thermistor bead 19. The diodes 17a-c and thermistor bead 19 are firmly sealed in place within the respective bores 15a-d by means of a silicon potting compound which enables the diodes 17a-c and thermistor 19 to be in intimate thermal contact with the silver mass 9.

A platinum wire electrode 21 which serves as the cathode of the transcutaneous oxygen probe is disposed on the axis of the central bore 13 and is sealed in place within a solid cylindrical mass 23 made of a rigid insulating material which in the preferred embodiment of the invention is glass. The lowermost end of the platinum wire 21 is coextensive with the lowermost end of the solid cylindrical rod 23, so that only the very tip of the wire 21 is exposed. The opposite end of the wire 21 is connected to a cable which extends from the probe through the horizontal bore in the lateral section 5 of the shell 3.

The silver mass 9 serves as the anode for the probe and a wire 25 is connected to the mass 9 and is also extended through the horizontal bore in the lateral section 5 of the shell 3.

The fixation ring 10 has stretched across its circular opening a barrier including an upper membrane 27 and a lower membrane 29. The membranes 27 and 29 are held in place by a single O-ring or snap ring 31. A circular cover ring 33 also supports the membranes 27 and 29 on the fixation ring 10. The snap ring 33 can be provided with a layer of an adhesive material 35 on its lowermost surface to insure adherence of the probe to the skin of the person whose oxygen blood content is being measured or monitored.

The upper membrane 27 is absorbent and acts as a spacer between the lower membrane 29 and an electrolytic solution 37, disposed between the upper surface of the membrane 27 and the lower surface of the anode silver mass 9. The upper membrane 27 is preferably made from a cellulose material which will absorb the electrolyte and the lower membrane 29 is made of an oxygen permeable, ion impermeable, material which in the preferred embodiment of the invention is polypropylene. Teflon or polyethylene can also be used for the lower membrane 29. The electrolyte 37, in the preferred embodiment of the invention, is ethylene glycol which is preferred because of its high boiling point which minimizes evaporation. Also, ethylene glycol does not leave deposits on the cathode as do other electrolytes made from salt solutions which deposits reduce the effective surface area of the cathode.

Figure 3:
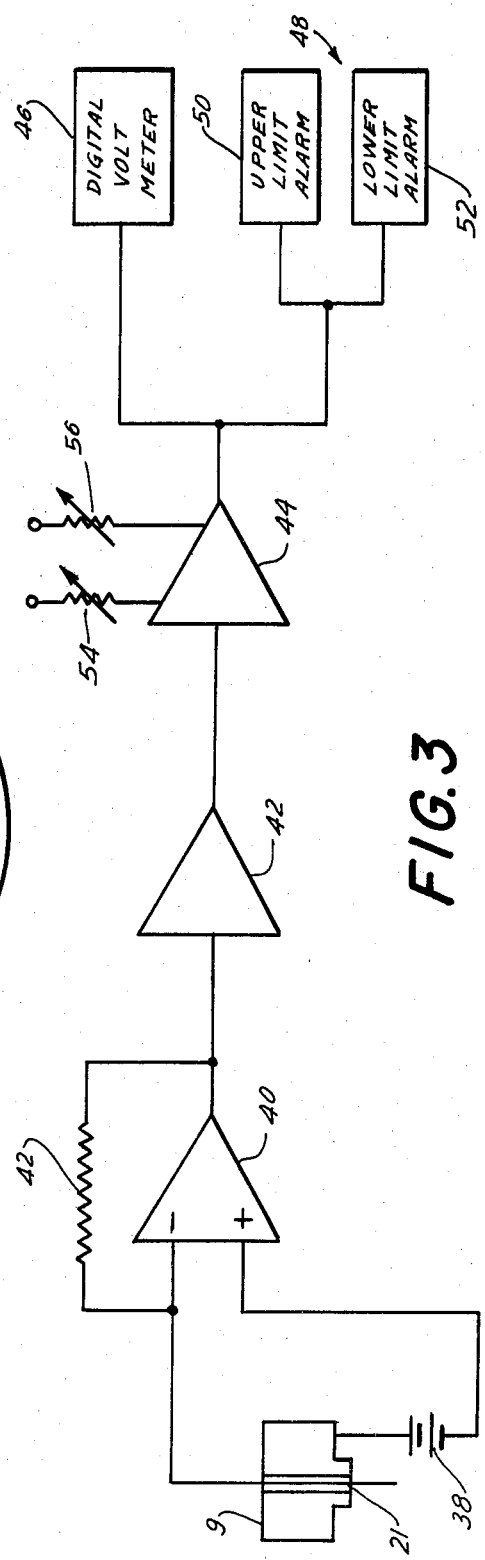
FIG. 3 is a schematic diagram of a circuit used with the preferred embodiment of the invention for measuring and monitoring blood oxygen content in a living being.

Referring now to FIG. 3 of the drawings, there is shown a schematic diagram of an electrical circuit used to measure and monitor blood oxygen content with the aid of the probe illustrated in FIGS. 1 and 2. The anode 9 of the sensor probe 1 is connected to the positive terminal of a DC power supply 38. In the preferred embodiment of the invention, the DC power supply 38 provides a substantially constant output voltage of 0.7 volts. The negative terminal of the supply is connected to the positive input of an amplifier 40. The cathode 21 of the sensor probe 1 is connected to the negative input of the amplifier 40. Feedback from the output of the amplifier 40 to the negative input is provided through resistor 42. The amplifier 40 has a voltage output proportional to the current flowing between the anode 9 and cathode 21. The output of the amplifier 40 is connected to the input of an isolation amplifier 42 which provides a high impedance separating the sensor probe 1, DC power supply 38 and amplifier 40 from a calibration amplifier 44, the output of which is connected to a volt meter 46, which includes a digital display, and an alert monitoring circuit 48 having an upper limit alarm 50 and a lower limit alarm 52.

The calibration amplifier 44 has a zero adjustment potentiometer control 54 and a gain adjustment potentiometer 56. Calibration is accomplished by first applying the sensor probe 1 to an environmental having zero oxygen content and setting the control 54 so that a zero reading is obtained on the display of the volt meter 46. The sensor probe 1 is then applied in an environment of known oxygen content and the gain control 56 of the calibration amplifier 44 is adjusted so that the display of the volt meter 46 provides a percentage oxygen reading equal to the known percentage of oxygen in the gain calibration environment.

Each of the upper and lower limit alarms 50 and 52 respectively, of the alert circuitry 48 includes a threshold circuit. The threshold circuit of the upper limit alarm 50 is adjusted so that if the output voltage of the amplifier 44 exceeds the threshold set into the upper limit alarm 50 which corresponds to an upper limit of acceptable blood oxygen content, an alarm will sound and an indicator also included in the upper limit alarm circuitry 50 will be energized to show that the upper oxygen limit has been exceeded. Similarly, if the output voltage of the amplifier 44 drops below a threshold set into the lower limit alarm circuitry 52, which corresponds to a lower limit of acceptable blood oxygen content, an alarm will sound and a lower limit alert indicator in the lower limit alarm 52, will indicate that blood oxygen content is below the minimum acceptable lower limit. Means can be provided in the upper and lower limit alarms 50 and 52 for adjusting the respective upper and lower threshold voltages at which the alarms will sound. Circuitry for accomplishing the alarm function and for varying the threshold limits will be known to those skilled in the art. In addition to the amplifier 42, the calibration amplifier 44 provides a high impedance to insure that the circuitry powering the alarms and indicators is isolated from the sensor probe 1 to insure patient safety.

As previously stated, it is desirable to warm the region of the skin where the sensor probe 1 is applied to promote vasodilation of the blood vessels and oxygen permeation through the skin. Depending upon the patient and environmental conditions, a constant temperature of between 41 and 44 degrees centigrade is generally selected as the optimum temperature at which to maintain the sensor probe 1. 41 degrees centrigrade is generally the accepted optimum capillary temperature but because of losses in the transmission of heat from the probe 1 through the skin to the capillaries, it is often necessary to maintain the probe temperature slightly above this level. A circuit for maintaining the sensor probe 1 at a constant preselected temperature and for measuring and monitoring the power required to maintain the constant preselected temperature for providing an indication of local perfusion factor, will now be described with reference to FIG. 4.

Figure 4:
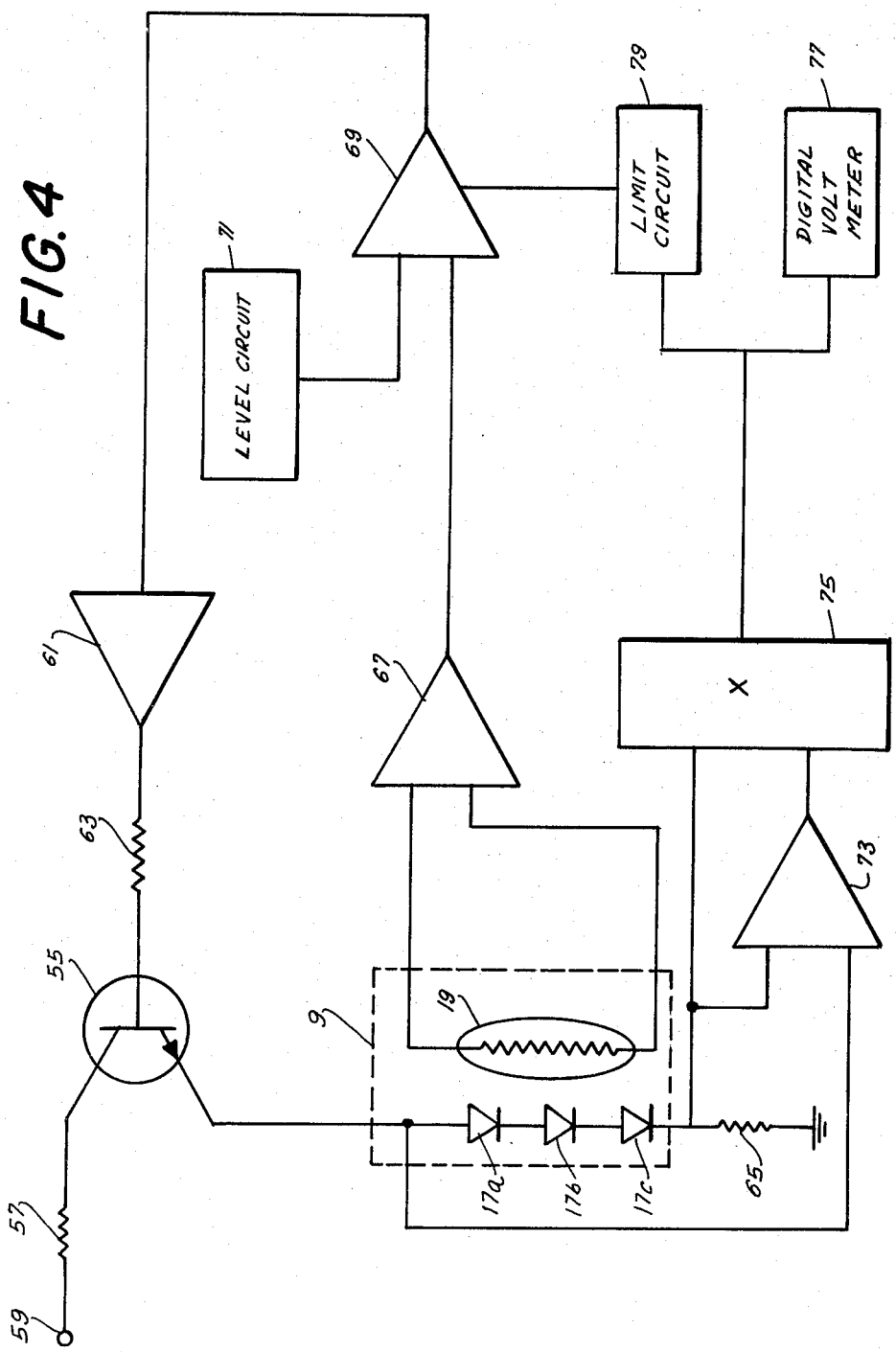
FIG. 4 is a schematic diagram of an electrical circuit used with the preferred embodiment of the invention for heating the probe of the invention to a constant predetermined temperature and measuring and monitoring the power required to maintain said constant temperature.

In FIG. 4 the silver anode 9 is shown schematically to encompass the heater diodes 17a, b and c and the thermistor bead 19. A source of positive DC potential (not shown) is applied to the collector of a transistor 55 through a resistor 57 at terminal 59. When the resistor 55 is rendered conducting by a positive voltage at the output of an amplifier 61 applied to the base of the transistor 55 through a resistor 63, current flows through the series diodes 17a, b and c and then to ground through a resistor 65 which, in the preferred embodiment of the invention, has a value on the order of 10 ohms. Heat emitted by the diodes 17a, b and c as a result of the current passing through them is conducted through the silver anode 9 to the thermistor bead 19. The voltage across the thermistor bead 19 varies as a function of the temperature of the silver anode 9 and is applied to the input of an amplifier 67. The voltage output of the amplifier 67 is proportional to the temperature of the silver anode and, hence, of the sensor probe 1.

The output voltage of the amplifier 67 which is proportional to probe temperature is applied to one input of a differential amplifier 69. A voltage level circuit 71 is connected to the other input of the differential amplifier 69. The voltage level circuit 71 applies to the amplifier 69 a constant reference voltage which can be set according to the desired temperature of the silver anode 9. Differences between the output voltage of the amplifier 67, which is an indication of the actual anode temperature, and the output voltage of the level setting circuit 71, which corresponds to the desired anode temperature, are reflected in the output of the amplifier 69 which is applied to the input of amplifier 61. In the absence of a positive voltage at the output of the amplifier 61, the transistor 55 is rendered non-conducting and no current is applied to the diodes 17a, b and c to heat the silver anode 9. When the output voltage of the amplifier 67 is less than the output voltage of the level setting circuit 71, thus indicating that the anode temperature is below the desired level set into the circuit 71, a positive output is generated at the output of amplifier 69 which is applied by amplifier 61 through the resistor 63 to the base of the transistor 55 to turn on the diode heater as previously described. Once temperature equilibrium is reached at the level set into the circuit 71, the voltage output of the amplifier 69 and, hence, of the amplifier 61, decreases until the transistor 55 is turned off.

The inputs of a differential amplifier 73 are connected across the series chain of diodes 17a, b and c, so that there is provided at the output of the amplifier 73 a voltage equal or proportional to the voltage across the diodes 17a, b and c. The output of the amplifier 73 is connected to one input of an analog multiplier circuit 75 which is commercially available. The other input of the multiplier circuit 75 is connected to the node between the resistor 65 and diode 17c. The voltage at the node is equal or proportional to the current flowing through the string of diodes 17a, b and c. Hence, the output of the multiplier circuit 75 is equal or proportional to the power dissipated in the diodes 17a, b and c, to heat the anode 9.

The ratio of the voltages respectively appearing at the multiplicand and multiplier inputs of the multiplier circuit 75, should not exceed a ratio of 100 to 1, if acceptable accuracy is to be achieved. By computing power in the diodes 17a, b and c from a multiplication of diode current and diode voltage, the parameters of the circuit components can be selected so that the ratio of diode voltage to diode current can be expected to be within the desired ratio. Where power is computed by squaring the diode current or voltage and multiplying it by a resistance factor, the ratio of the multiplicand to multiplier will often exceed the ratio limit necessary for accurate results.

The output of the multiplier 75 is a voltage equal or proportional to diode power. The circuit components in the preferred embodiment are selected so that the output voltage of the multiplier 75 is equal to diode power. However, as will be appreciated by those skilled in the art, a voltage output proportional to diode power may be obtained at the output of the multiplier 75 and this voltage may be applied to an appropriate scaling amplifier to obtain a voltage of magnitude equal to the magnitude of the diode power.

The voltage indicative of diode power is applied to the input of a volt meter 77 having a digital display to provide a visual indication of the amount of power being dissapated in the diodes 17a, b and c, and therefore also providing an indication of the local perfusion factor. As previously stated, the local perfusion factor can be correlated to mean blood pressure and provides a noninvasive means for continuously measuring blood pressure.

The voltage output of the multiplier 75 is also applied to a heater limit circuit 79, which prevents the diode heater in the probe 1 from heating the probe beyond a safe level. The application of excessive power to the diodes 17a, b and c raises a risk of burning the skin of the patient. The heater limit circuit 79 includes means for setting a threshold level of maximum power to be applied to the diodes 17a, b and c. The maximum power level can be set by the physician or technician operating the blood oxygen measuring apparatus of the invention and, in the preferred embodiment of the invention, will usually be set somewhere in the range of 350 milliwatts to 800 milliwatts. The adjusted output voltage of the circuit 79, which is equal or proportional to the maximum safe milliwatt heater output that has been selected, is applied to an input of amplifier 69 to decrease the output of the amplifier 69 when the power dissipated in the diodes 17a, b and c exceeds the maximum safe output, thereby turning off the transistor 55.

It is to be appreciated that variations and alterations to and modifications of the preferred embodiment of the invention disclosed herein can be made without departing fom the spirit and scope of the invention which is set forth in the following claims.

What is claimed is:

1. In a transcutaneous gas measurement probe including first and second electrodes, means for maintaining an electrolytic solution in contact with said first and second electrodes, means permeable to the gas to be measured in contact with said electrolytic solution and adapted to contact the surface at which said gas is transcutaneous, and means for maintaining said probe at substantially constant temperature, the improvement wherein said temperature maintaining means comprises
   a semi-conductor device mounted in thermal transmitting relationship to said probe,
   heater circuit means connected to said semi-conductor device for applying a controlled amount of current thereto for maintaining the temperature of said probe at a substantially constant predetermined temperature,
   a first voltage producing means connected in parallel with said semi-conductor device for producing a first voltage having a magnitude proportional to the voltage across said semi-conductor device,
   a second voltage producing means operatively connected to said semi-conductor device so as to conduct a current passing through said semi-conductor device for producing a second voltage having a magnitude proportional to said current,
   a multiplier circuit having a first input operatively connected to said first voltage producing means and a second input operatively connected to said second voltage producing means and an output at which there is produced a product voltage having a magnitude proportional to the product of the magnitudes of the first and second voltages.

2. Apparatus according to claim 1 further including a temperature sensor connected to said heater circuit means, and in thermal transmitting relationship to said probe, said heater circuit means reducing the flow of said current to said semi-conductor device when said probe temperature is increased and increasing said current flow to said semi-conductor device when said probe temperature is decreased.

3. Apparatus according to claim 2 further comprising a reference circuit means operatively connected to said heater circuit means for storing a signal proportional to a predetermined temperature at which it is desired to maintain said probe, and comparison means operatively connected to said reference circuit means and to said sensor, said heater circuit means being operatively connected and responsive to said comparison means for regulating said current flow to maintain said probe at said predetermined temperature.

4. Apparatus according to claim 1 further comprising means responsive to said multiplier circuit for displaying a number proportional to the magnitude of the power applied to said semi-conductor device.

5. Apparatus for measuring and monitoring blood gas content comprising
   a transcutaneous gas measurement probe including first and second electrodes, said first electrode being formed of a thermally conductive material and having a mass substantially greater than the mass of said second electrode,
   a diaphragm permeable to the gas to be measured and enclosing a region between said first and second electrodes and adapted to confine an electrolytic solution therein,
   means for applying a voltage across said first and second electrodes,
   a semi-conductor device thermally conductively coupled to said first electrode,
   a temperature sensor element thermally conductively coupled to said first electrode, said temperature sensor element having an output voltage with a magnitude proportional to the temperature of said first electrode, means for selectively applying an electric current to said semi-conductor device, said selective applying means being responsive to said temperature sensor output voltage for applying said current only when said temperature sensor output voltage is below a predetermined level, means for providing a first voltage proportional to the voltage across said semi-conductor device, means for producing a second voltage having a magnitude proportional to the current flowing through said semi-conductor device, means for producing a product voltage having a magnitude equal to the product of said first and second voltage magnitudes, and means for displaying a magnitude dependent on said poduct voltage magnitude.

6. Apparatus according to claim 5 further comprising alert circuit means having a predetermined threshold voltage stored therein, said alert circuit means being responsive to said product voltage for generating an alarm signal when said product voltage is beyond a tolerance corresponding to said threshold voltage.

7. Apparatus according to claim 5 further comprising means for comparing said product voltage with a predetermined voltage indicative of a maximum predetermined limit for the power dissipated in said semi-conductor device, said selective applying means being responsive to said comparing means for interrupting the flow of current to said semi-conductor device when said maximum power limit is exceeded by the power applied to said semi-conductor device.

8. A method for measuring local perfusion factor in a living body comprising applying a probe heated by an electrically energized semi-conductor device to the skin surface of the body, obtaining an electrical signal having a magnitude indicative of the temperature of said probe, applying an electric current to the semi-conductor device in response to said temperature indicative signal for maintaining the probe at a predetermined constant temperature, measuring the power applied to said probe for maintaining said constant temperature by multiplying the magnitude of the current applied to heat said semi-conductor device by the magnitude of the voltage developed across said semi-conductor device.

* * * * *